(12) United States Patent
Holladay et al.

(10) Patent No.: US 7,772,412 B2
(45) Date of Patent: Aug. 10, 2010

(54) METHODS FOR DEHYDRATION OF SUGARS AND SUGAR ALCOHOLS

(75) Inventors: Johnathan E. Holladay, Kennewick, WA (US); Jianli Hu, Kennewick, WA (US); Xinjie Zhang, Burlington, MA (US); Yong Wang, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 269 days.

(21) Appl. No.: 11/341,968

(22) Filed: Jan. 26, 2006

(65) Prior Publication Data

US 2007/0173654 A1 Jul. 26, 2007

(51) Int. Cl.
*A61K 31/34* (2006.01)
*C07D 493/04* (2006.01)

(52) U.S. Cl. ...................... 549/464; 514/470

(58) Field of Classification Search ........ None
See application file for complete search history.

(56) References Cited

U.S. PATENT DOCUMENTS

| 3,160,641 | A | | 12/1964 | Hartmann et al. |
| 4,297,290 | A | | 10/1981 | Stockburger |
| 4,408,061 | A | | 10/1983 | Salzburg et al. |
| 4,506,086 | A | | 3/1985 | Salzburg et al. |
| 4,564,692 | A | | 1/1986 | Feldmann et al. |
| 4,861,513 | A | | 8/1989 | Lueders et al. |
| 5,093,535 | A | * | 3/1992 | Harrison et al. ............ 568/881 |
| 6,013,812 | A | | 1/2000 | Haas et al. |
| 6,124,443 | A | * | 9/2000 | Darsow ................... 536/18.5 |
| 6,392,062 | B1 | | 5/2002 | Haas |
| 6,407,266 | B2 | | 6/2002 | Bhatia |
| 6,639,067 | B1 | | 10/2003 | Brinegar et al. |
| 6,689,892 | B2 | | 2/2004 | Andrews et al. |
| 6,693,209 | B2 | | 2/2004 | Van Es et al. |
| 7,439,352 | B2 | | 10/2008 | Moore et al. |
| 2002/0052516 | A1 | | 5/2002 | Moore et al. |
| 2003/0097028 | A1 | | 5/2003 | Fuertes |
| 2003/0229235 | A1 | | 12/2003 | Bhatia |
| 2004/0030161 | A1 | | 2/2004 | Bhatia |
| 2004/0110969 | A1 | | 6/2004 | Fleche et al. |
| 2004/0110994 | A1 | | 6/2004 | Bhatia |

FOREIGN PATENT DOCUMENTS

| CA | 1178288 | | 11/1984 |
| EP | 0061055 | A1 | 9/1982 |
| EP | 0201067 | A2 | 11/1986 |
| EP | 0380402 | A1 | 8/1990 |
| EP | 0915091 | A2 | 5/1999 |
| EP | 1179535 | A1 | 2/2002 |
| EP | 1179536 | A1 | 2/2002 |
| WO | 9721697 | A1 | 6/1997 |
| WO | 2000014081 | A1 | 3/2000 |
| WO | 0041985 | | 7/2000 |
| WO | 0172136 | A1 | 10/2001 |
| WO | 0194352 | A1 | 12/2001 |
| WO | 0239957 | A2 | 5/2002 |
| WO | 03022064 | A1 | 3/2003 |
| WO | 03089436 | A1 | 10/2003 |
| WO | 03089445 | A1 | 10/2003 |
| WO | 2005047228 | A1 | 5/2005 |

OTHER PUBLICATIONS

2006 Chemical Abstracts Catalog, published 2006 by Chemical Abstracts Service. p. 52.*
Fleche, et al., "Isosorbide" Starch/Starke, vol. 38, 1986, pp. 26-30.

* cited by examiner

*Primary Examiner*—Eric S Olson
(74) *Attorney, Agent, or Firm*—Wells St. John P.S.

(57) ABSTRACT

The invention includes a method of dehydration of a sugar using a dehydration catalyst and a co-catalyst within a reactor. A sugar is introduced and $H_2$ is flowed through the reactor at a pressure of less than or equal to about 300 psig to convert at least some of the sugar into an anhydrosugar product. The invention includes a process for producing isosorbide. A starting material comprising sorbitol is flowed into a reactor. $H_2$ is counter flowed through the reactor. The starting material is exposed to a catalyst in the presence of a co-catalyst which comprises at least one metal. The exposing is conducted at a hydrogen pressure of less than or equal to 300 psig within the reactor and the hydrogen removes at least some of any water present during the exposing and inhibits formation of colored byproducts.

15 Claims, No Drawings

METHODS FOR DEHYDRATION OF SUGARS AND SUGAR ALCOHOLS

CONTRACTUAL ORIGIN OF THE INVENTION

This invention was made with Government support under contract DE-AC0676RLO-1830, awarded by the U.S. Department of Energy. The Government has certain rights in this invention.

TECHNICAL FIELD

The invention pertains to methods of dehydrating sugars and methods of producing isosorbide.

BACKGROUND OF THE INVENTION

Dehydration products resulting from dehydration of sugars have numerous applications including but not limited to use as emulsifiers in products such as food and cosmetics, and as biodegradable surfactants. Sugar dehydration products can additionally be useful for production of various medication therapeutics and high-property polymers.

Conventional processes for catalytic dehydration of sugars to produce anhydrosugars can often result in production of a colored product. Such reactions can also result in formation of dark colored polymers which are retained on particular catalysts and can result in catalyst fouling and deactivation. Where dark colored product is produced, the product typically must undergo additional processing to decolorize the product prior to use and/or further processing.

It is desirable to develop alternative methods for conducting sugar dehydration reactions for production of anhydrosugars.

SUMMARY OF THE INVENTION

In one aspect, the invention encompasses a method of dehydration of a sugar. The method includes providing a dehydration catalyst within a reactor, and also providing a co-catalyst which includes a support material and a metal within the reactor. A sugar is introduced into the reactor and $H_2$ is flowed through the reactor. The sugar is exposed to the catalyst in the presence of the co-catalyst at a $H_2$ pressure of less than or equal to about 300 psig to convert at least some of the sugar into an anhydrosugar product. The reaction is conducted at an overall pressure of less than or equal to 500 psig and the flow of $H_2$ through the reactor removes water from the reactor during the exposing.

In one aspect, the invention encompasses a process for producing isosorbide. A starting material comprising sorbitol is flowed into a reactor. $H_2$ is counter flowed through the reactor. The starting material is exposed to a catalyst in the presence of a co-catalyst which comprises at least one metal selected from the group consisting of Pd, Pt, Ni, Co, Ru, Re, Rh, Ir, and Fe. The exposing is conducted at a hydrogen pressure of less than or equal to 300 psig within the reactor and the hydrogen removes at least some of any water present during the exposing and inhibits formation of colored byproducts.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

In general, the invention pertains to methods for processing sugars and for production of anhydrosugars. The methodology of the invention can be particularly useful and advantageous in that the anhydrosugar product from the dehydration reactions in accordance with the invention can have significantly reduced byproduct content relative to conventional dehydration methodology. In particular, the reactions of the invention can minimize or eliminate production of colored byproduct, thereby minimizing or eliminating additional processing for decolorization. The reduction in byproduct afforded by the methodology of the invention additionally provides increased catalyst lifetime relative to conventional techniques.

In conventional sugar dehydration processing, a mineral acid catalyst is typically utilized for batch processing of sugar to produce anhydrosugars and/or dianhydrosugar alcohols. Alternatively, solid acid catalysts can be utilized, however, the lifetime of such catalysts is short since the acid catalyst can become fouled and/or deactivated during the dehydration reaction. Such fouling and deactivation appears to be caused at least in part by production of oligomeric and/or polymeric materials under the reaction conditions utilized. These oligomers/polymers can be present as contaminants in the resulting product. Typically a decolorization process is conducted for removal of byproducts within the anhydrosugar product.

Dark-colored brown/black polymer material produced during acid catalyzed dehydration reactions appears to be due to formation of carbon-carbon double bonds and/or carbon-oxygen double bonds or charcoal-like materials. These double-bond type molecules can be thermally polymerized at elevated temperatures to form large polymers. In accordance with the invention, sugar dehydration reactions are conducted in the presence of a co-catalyst which is capable of reducing double-bonds and/or inhibiting the formation of double-bonds, thereby reducing or eliminating formation of the undesirable colored polymer materials.

Sugar dehydration methodology of the invention can typically comprise providing a dehydration catalyst within a reactor and additionally providing a co-catalyst within the reactor. Dehydration catalysts which can be utilized include but are not limited to solid acid catalysts, mineral acid catalysts, and combinations thereof. Where a solid acid catalyst is utilized, such catalysts can comprise of one or more materials selected from heteropolyacids, meso-porous silicas, acid clays, sulfated zirconia, molecular sieve materials, cation exchange resins, zeolites, and combinations thereof. Exemplary mineral acid catalysts which can be utilized independently or together with one or more solid acid catalyst material include but are not limited to sulfuric acid, phosphoric acid and hydrochloric acid.

Co-catalysts which can be utilized in conjunction with the acid catalyst in accordance with the invention are hydrogenation catalysts which act in the presence of hydrogen, and are preferably hydrogenation catalysts which have activity at low or moderate temperatures. More preferably, the hydrogenation catalysts of the invention are able to effectively co-catalyze reactions conducted at room temperature. Typically, co-catalysts in accordance with the invention will comprise a metal and a support material and can comprise multiple metals and/or multiple support materials. Although not limited to particular metals, the co-catalysts can preferably comprise a metal selected from Pd, Pt, Ni, Co, Ru, Re, Rh, Ir, Fe, and combinations thereof. Palladium can be especially preferable due to its ability to hydrogenate in the presence of hydrogen at room temperature.

The support material comprised by the co-catalyst in accordance with the invention is not limited to a particular material and in particular instances will comprise elemental carbon. Alternative support materials include but are not limited to zirconia ($ZrO_2$), titania ($TiO_2$), niobia ($Nb_2O_5$), silica, and tin.

The solid acid catalysts in accordance with the invention can additionally be supported by a thermo-stable support material such as for example, silica, tin oxide, niobia, zirconia, titania, carbon, or mixtures thereof. Although the catalyst and co-catalyst described above are independent and can be provided to the reactor independently, the invention additionally encompasses utilization of uniform bi-functional catalyst material which comprises both an acid catalyst function and a hydrogenation co-catalyst. Exemplary bi-functional catalysts can comprise for example AMBERLYST® CH10 or AMBERLYST® CH28 (Rohm and Haas Company, Philadelphia, Pa.).

Sugar dehydration reactions in accordance with the invention can be conducted in a variety of reactor types. The reactor utilized can be a batch reactor or preferably can be a reactor for performing continuous dehydration processing. Appropriate reactors which can be utilized are available and known to those skilled in the art.

A starting material containing the sugar or sugars to undergo dehydration is introduced into the reactor prior to, simultaneously with, or after providing the catalyst and co-catalyst into the reactor. Where continuous reaction conditions are utilized, the introduction of starting material can preferably comprise flowing the starting material through a reactor containing the catalyst and the co-catalyst. The starting material is not limited to a particular form and can be one or more sugars and/or anhydrosugars (also referred to as sugar alcohols, or anhydrosugar alcohols) in an absence of solvent or can be a mixture comprising a solvent and one or more sugars and/or sugar alcohols.

The invention is not limited to any particular sugar or anhydrosugar starting material and can be utilized for dehydration of a single sugar, a single anhydrosugar and mixtures containing one or more sugar and/or anhydrosugars. The invention can be particularly useful for dehydration of sorbitol or production of sorbitan and/or isosorbide, or for further dehydration of the anhydrosugar 1, 4-sorbitan to isosorbide. Other sugars and anhydrosugars of particular interest for utilization as starting sugars for dehydration in accordance with the invention include but are not limited to xylitol, arabinitol, mannitol, and mixtures thereof.

Reaction methodology in accordance with the invention includes flowing $H_2$ through the reactor. The amount of $H_2$ provided is not limited to a particular quantity and can depend upon for example, the particular type of reactor utilized, the flow rate/amount of starting material, and other reaction conditions. Preferably, the reaction is conducted utilizing a $H_2$ pressure of less than or equal to about 300 psig. Although the overall reaction pressure is similarly not limited to a particular value, exposing of the starting material to the catalyst and co-catalyst is typically conducted at an overall pressure of less than or equal to about 500 psig. In particular applications, it can be preferable that the total pressure within the reactor is less than or equal to 300 psig and, in some instances, will be less than or equal to 100 psig. Accordingly, the $H_2$ pressure can be adjusted to accommodate the desired overall reaction pressure.

Although the methodology of the present invention is not limited to particular reagent input or flow scheme, the flowing of $H_2$ through the reactor can preferably be conducted such that the hydrogen flow removes some or all of any water present during the reaction. Where continuous dehydration processing is utilized, the $H_2$ can preferably be provided in a counter flow through the reactor relative to the flow of starting material through the reactor.

The dehydration reactions in accordance with the invention are additionally not limited to any particular temperature. Preferably, the dehydration reactions can be conducted within the range of temperature of from about 110° C. to about 170° C. However, in particular instances, the reactions can be conducted at room temperature.

By utilizing an acid catalyst as described above in combination with a hydrogenation co-catalyst, dehydration reactions in accordance with the invention can be utilized for reducing or eliminating the oligomeric or polymeric materials in the dehydration product. Such methodology is successful for producing colorless product as produced such that an additional decolorization processing can be eliminated. The combination of acid catalyst and hydrogenation catalyst additionally minimizes or avoids catalyst fouling, and minimizes catalyst deactivation, thereby increasing the catalyst lifetime. Accordingly, dehydration processes in accordance with the invention are both more cost effective and efficient than conventional dehydration methodology.

EXAMPLES

A series of seven dehydration processes, identified as Reactions 1-7, were conducted independently utilizing the same reaction system at varying reaction conditions. Three comparative studies were also performed and are identified as Reactions A-C. The comparative reactions were also conducted independently in the reaction system utilized for Samples 1-7.

The methodology for performing dehydration reactions for Reactions 1-7, and Reactions A-C was as follows. Starting material, catalyst and co-catalyst were each added into a glass reactor. The reactor was put into a high-pressure stainless steel autoclave and the system was charged with hydrogen. The system was heated to 160° C. over a time period of 45 minutes and was then maintained at 160° C. for four hours for Samples 1-3 and A-C, for six hours for Samples 4 and 5, or for 20 hours for Samples 6 and 7. The resulting mixture was filtered utilizing a 0.2 micron filter. The filtered product was then analyzed utilizing HPLC. The reaction conditions for each of Reactions 1-7 and comparative Reactions A-C are presented in Table I. The hydrogen pressure was 1500 psig, 300 psig, or 30 psig, as indicated in the table.

TABLE I

| | | Dehydration Reaction Conditions | | | | |
|---|---|---|---|---|---|---|
| Reaction ID | Raw material | Catalyst | Temp (° C.) | Time (hr) | Pressure (psig) | Gas |
| 1 | 30 g sorbitol | 3.0 g HPW + 0.5 g Pd/C | 160 | 4 | 1500 | $H_2$ |
| 2 | 30 g sorbitol | 3.0 g HPW + 0.5 g Pd/C | 160 | 4 | 300 | $H_2$ |

TABLE I-continued

Dehydration Reaction Conditions

| Reaction ID | Raw material | Catalyst | Temp (° C.) | Time (hr) | Pressure (psig) | Gas |
|---|---|---|---|---|---|---|
| 3 | 30 g sorbitol | 3.0 g HPW + 0.5 g Pd/C | 160 | 4 | 30 | $H_2$ |
| 4 | 30 g sorbitol | 6.0 g wet Amberlyst 36 + 0.5 g Pd/C | 160 | 6 | 30 | $H_2$ |
| 5 | 30 g sorbitol | 5.0 g wet Nafion 50 + 0.1 g $PdCl_2$ | 160 | 6 | 30 | $H_2$ |
| 6 | 10 g sorbitol + 20 g $H_2O$ | 1 g wet Nafion 50 + 0.5 g Pd/C | 160 | 20 | 30 | $H_2$ |
| 7 | 30 g sorbitol + 70 g $H_2O$ | 3.0 g HPW + 0.5 g Pd/C | 160 | 20 | 30 | $H_2$ |
| A | 30 g sorbitol | 3.0 g HPW + 0.5 g C | 160 | 4 | 1500 | $H_2$ |
| B | 30 g sorbitol | 3.0 g HPW + 0.1 g $PdCl_2$ | 160 | 4 | 1500 | $H_2$ |
| C | 30 g sorbitol | 3.0 g HPW + 0.5 g Pd/C | 160 | 4 | 30 | Ar |

As set forth in Table I, Reactions 1-5, and comparative Reactions A-C were each conducted utilizing sorbitol in absence of solvent. High purity sorbitol was utilized in each instance. For Reactions 6 and 7, high purity sorbitol in the amount indicated, was added to water to form a mixture prior to introduction into the presence of the indicated catalyst. The acid catalysts utilized for the study presented in Table I were $H_3PW_{12}O_{40}$ (phosphortungstic acid, HPW), NAFION® 50 (E.I. Du Pont Nemours and Company, Wilmington, Del.), or AMBERLYST®36 (Rohm & Haas Company, Philadelphia, Pa.). The co-catalyst utilized was either palladium on elemental carbon support material or $PdCl_2$. The results and observations for each of the ten reactions are presented in Table II.

TABLE II

Dehydration Reaction Results and Observations

| Reaction ID | Sorbitol conversion (%) | 3,6-sorbitan (%) | 1,4,-sorbitan (%) | Isosorbide (%) | Other* (%) | Product color |
|---|---|---|---|---|---|---|
| 1 | 100 | 0 | 6.19 | 64.55 | 19.55 | Clear |
| 2 | 100 | 0 | 8.34 | 65.47 | 15.96 | Clear |
| 3 | 100 | 0 | 11.24 | 62.21 | 15.16 | Clear |
| 4 | 100 | 0 | 2.1 | 72.68 | 13.79 | Clear |
| 5 | 100 | 0.61 | 55.76 | 24.89 | 7.63 | Clear |
| 6 | 100 | 0 | 29.71 | 45.88 | 8 | Clear |
| 7 | 59.26 | 5.73 | 70.33 | 13.06 | 0 | Clear |
| A | 100 | 0 | 4.22 | 45.93 | 43.31 | Black |
| B | 100 | 0 | 4.28 | 45.25 | 43.59 | Black |
| C | 100 | 0 | 2.24 | 70.5 | 16.9 | Black |

*Other indicates un-recovered or undetected material

As indicated, the filtered product for each of Samples 1-7 was clear, while the comparative Example A-C produced dark-colored/black material product. It is noted that the co-catalyst $PdCl_2$ utilized in Sample 5, comprised highly dispersed palladium while the $PdCl_2$ utilized in comparative Reaction B comprised non-highly dispersed Pd. Accordingly, high dispersion of Pd appears to be a factor for production of clear product material. It is also noted that high pressure (1500 psig) results in a high content of other material, where "other" refers to material that was un-recovered and/or undetected by HPLC. Low pressure however (from about 30 psig through about 200 psig) results in very low content of other/undetectable materials. Accordingly, it can be preferable to conduct the dehydration reactions of the invention at hydrogen pressures of less than or equal to about 300 psig.

The results presented in Table II additionally indicate that, while use of argon in place of $H_2$ at low pressure (30 psig) results in a relatively small difference in the amount of other/undetectable materials, the resulting product from the argon study (Reaction C) is black, indicating the presence of oligomeric/polymeric materials. The results also indicate that the presence of water/solvent in the starting material did not influence, or had minimal influence upon the formation of clear products.

The results above indicate that various acid catalysts can be successfully utilized in the presence of co-catalysts in accordance with the invention to produce sugar dehydration products with minimal or no colored byproduct present after filtration. Accordingly, processing in accordance with the invention can eliminate decolorization processing and allow increased overall reaction efficiency. The results also indicate successful selectivity for 1,4-sorbitan production and resulting isosorbide. Due to the decreased or eliminated production of oligomers/polymers during the dehydration reaction in accordance with the invention, decreased acid catalyst fouling and deactivation occurs, thereby increasing catalyst lifetime. Accordingly, the overall methodology of the invention allows product selectivity reaction efficiency and cost-effective production of anhydrosugar products.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

The invention claimed is:

1. A method of dehydration of a sugar or sugar alcohol, comprising:
   providing a dehydration catalyst within a reactor, the dehydration catalyst being selected from the group consisting of solid acid catalysts and mineral acid catalysts;
   providing a co-catalyst comprising a support material and a metal within the reactor;
   introducing a sugar or sugar alcohol to the reactor in the absence of any solvent;
   flowing $H_2$ through the reactor; and
   exposing the sugar or sugar alcohol to the catalyst in the presence of the co-catalyst at a $H_2$ pressure of less than or equal to about 300 psig to convert at least some of the sugar or sugar alcohol into a bicyclic ether anhydrosugar product, the exposing being conducted at an overall pressure of less than or equal to 500 psig, the flowing $H_2$ through the reactor removing all water from the reactor during the exposing.

2. The method of claim 1 wherein the total pressure is less than or equal to 300 psig.

3. The method of claim 1 wherein the total pressure is less than or equal to 100 psig.

4. The method of claim 1 wherein the metal is selected from the group consisting of Pd, Pt, Ni, Co, Ru, Re, Rh, Ir, and Fe.

5. The method of claim 1 wherein the support material comprises elemental carbon.

6. The method of claim 1 wherein the dehydration catalyst comprises a solid acid catalyst.

7. The method of claim 6 wherein the solid acid catalyst is a resin.

8. The method of claim 6 wherein the solid acid is supported by a thermo-stable support material comprising at least one member of the group consisting of silica, tin oxide, niobia, zirconia, titania and carbon.

9. The method of claim 1 wherein the dehydration catalyst comprises at least one member of the group consisting of a heteropoly acids, meso-porous silicas, acid clays, sulfated zirconia, molecular sieve materials, anion exchange resins, and zeolites.

10. The method of claim 1 wherein the introducing a sugar or sugar alcohol into the reactor comprises flowing a mixture containing the sugar or sugar alcohol into the reactor.

11. The method of claim 10 wherein the flowing $H_2$ comprises counter-flowing $H_2$ relative to the flow of the mixture containing the sugar or sugar alcohol.

12. A process of producing isosorbide, comprising:
flowing a starting material comprising sorbitol into a reactor;
counter-flowing H2 into the reactor; and
in the absence of water, exposing the starting material to a catalyst selected from the group consisting of solid acid catalysts and mineral acid catalysts, in the presence of a co-catalyst comprising at least one metal selected from the group consisting of Pd, Pt, Ni, Co, Ru, Re, Rh, Ir, and Fe, the exposing being conducted at a hydrogen pressure of less than or equal to 300 psig within the reactor and a total pressure of less than or equal to 500 psig, the H2 removing at least some of any water formed during the exposing and inhibiting formation of colored byproducts.

13. The method of claim 12 wherein the catalyst is a solid acid catalyst.

14. The method of claim 12 wherein the catalyst is a mineral acid catalyst.

15. The method of claim 12 wherein the co-catalyst comprises Pd on a carbon support.

* * * * *

UNITED STATES PATENT AND TRADEMARK OFFICE
CERTIFICATE OF CORRECTION

PATENT NO. : 7,772,412 B2  
APPLICATION NO. : 11/341968  
DATED : August 10, 2010  
INVENTOR(S) : Holladay et al.

Page 1 of 1

It is certified that error appears in the above-identified patent and that said Letters Patent is hereby corrected as shown below:

Column 5, Table II, Row 3, Line 2 – Replace "3.6-" with -- 3,6- --.

Column 5, Table II, Row 4, Line 2 – Replace "1.4.-" with -- 1,4,- --.

Signed and Sealed this

Fourteenth Day of December, 2010

David J. Kappos  
*Director of the United States Patent and Trademark Office*